(12) United States Patent
Murphy et al.

(10) Patent No.: US 10,433,820 B2
(45) Date of Patent: Oct. 8, 2019

(54) BIOPSY TRANSPORT DEVICE AND METHOD

(71) Applicants: Ronan Murphy, Toronto (CA); Sabrina Mattiassi, Brampton (CA); Kieran P. Murphy, Toronto (CA)

(72) Inventors: Ronan Murphy, Toronto (CA); Sabrina Mattiassi, Brampton (CA); Kieran P. Murphy, Toronto (CA)

(*) Notice: Subject to any disclaimer, the term of this patent is extended or adjusted under 35 U.S.C. 154(b) by 0 days.

(21) Appl. No.: 15/293,837

(22) Filed: Oct. 14, 2016

(65) Prior Publication Data

US 2017/0105708 A1    Apr. 20, 2017

Related U.S. Application Data

(60) Provisional application No. 62/241,925, filed on Oct. 15, 2015.

(51) Int. Cl.
| | |
|---|---|
| *G01N 1/00* | (2006.01) |
| *A61B 10/00* | (2006.01) |
| *A01N 1/02* | (2006.01) |
| *A01N 1/00* | (2006.01) |

(52) U.S. Cl.
CPC ............ *A61B 10/0096* (2013.01); *A01N 1/00* (2013.01); *A01N 1/0242* (2013.01); *A01N 1/0273* (2013.01)

(58) Field of Classification Search
CPC ...................................................... G01N 33/00
See application file for complete search history.

(56) References Cited

U.S. PATENT DOCUMENTS

| 4,282,986 A * | 8/1981 | af Ekenstam | A61M 5/282 222/1 |
| 4,376,634 A * | 3/1983 | Prior | G01N 33/579 422/562 |
| 5,429,803 A * | 7/1995 | Guirguis | A61B 10/007 422/419 |

OTHER PUBLICATIONS

Sehn JK, Gilula LA. Percutaneous needle biopsy in diagnosis and identification of causative organisms in cases of suspected vertebral osteomyelitis. European Journal of Radiology. May 2012; 81(5): 940-946.
Garg V, Kosmas C, Young PC, Togaru UK, Robbin MR. Computed tomography-guided percutaneous biopsy for vertebral osteomyelitis: a department's experience. Journal of Neurosurgery. Aug. 2014; 37(2):E10.

(Continued)

*Primary Examiner* — Jyoti Nagpaul
(74) *Attorney, Agent, or Firm* — Perry + Currier Inc.

(57) ABSTRACT

A device and method for preserving organisms (e.g. causative organisms in a case of osteomyelitis) in a biopsy sample during transport or storage in a manner which obviates or mitigates deleterious effects of lengthy periods of transport or storage on the success rate of determining the identity of the organism and subsequent testing. The device includes a reservoir which contains a transport medium, an outlet for releasable connection with a biopsy sample housing (e.g. a syringe with a luer connector element) containing a biopsy sample, and a closure member to seal the outlet before use. The transport medium can be delivered from the reservoir to the syringe, when the two are connected, and the reservoir-syringe unit can be transported as a sealed unit.

11 Claims, 7 Drawing Sheets

(56) References Cited

OTHER PUBLICATIONS

Heyer CM, Al-Hadari A, Mueller K, Stachon A, Nicolas V. Effectiveness of CT-Guided Percutaneous Biopsies of the Spine: An Analysis of 202 Examinations. Academic Radiology. Jul. 2008; 15(7): 901-911.
Rieneck K, Hansen SE, Karle A, Gutschik E. Microbiologically verified diagnosis of infectious spondylitis using CT-guided fine needle biopsy. APMIS. Aug. 15, 1996; 104(7-8):755-762.
Lecouvet F, Irenge L, Vandercam B, Nzeusseu A, Hamels S, Gala J. The etiologic diagnosis of infectious discitis is improved by amplification-based DNA analysis. American College of Rheumatology. Sep. 2004; 50(9):2985-2994.

* cited by examiner

BIOPSY TRANSPORT DEVICE AND METHOD

CROSS-REFERENCE TO RELATED APPLICATIONS

This application claims the benefit of U.S. provisional application 62/241,925, filed Oct. 15, 2015, under 35 U.S.C. 119(e), the entirety of which is incorporated herein by reference.

FIELD

The present invention relates to a device and method for transporting or storing biopsy samples.

BACKGROUND

Osteomyelitis is an infection and inflammation of the bone or bone marrow that can be caused by a number of different causative organisms. Bone biopsy procedures are the gold standard for the diagnosis of osteomyelitis because the procedures can determine the causative organism causing a particular case of osteomyelitis. Determination of the causative organism is essential for developing a proper treatment plan.

Bone samples can be obtained through either an open biopsy or through an image-guided percutaneous biopsy. The sample taken could be an aspiration of the bone, a core bone sample, or purulent fluid from an abscess. Once retrieved, a common practice is to place the biopsy material in a dry, sterile tube or in a formalin solution. The sample may then be subjected to histological and microbiological examination.

In microbiology, a sample may undergo microscopy, culture, and polymerase chain reaction analysis, among other tests, for the identification of the causative organism. In most cases, the causative organism is not easily determined. A retrospective study with "the largest series of consecutive percutaneous spinal biopsies" found that the success rate of determining the causative organism from culture is about 30%[1]. Other studies though have found the success rate to be as low as 19%[2] or 21%[3].

Studies which had unusually high success rates, such as 57% from Rieneck et al.[4], or 74% from Lecouvet et al.[5], all involved immediate specimen testing without a lengthy transportation period beforehand. In most cases, however, specimens are not tested immediately but are usually held in transit for several hours before being analysed.

Cases in which bone biopsy specimens experience transport for lengthy periods of time tend to result in a lower rate of successful identification of the causative organism behind a case of osteomyelitis.

SUMMARY

The present invention is intended to provide a novel device and method for preserving organisms (such as causative organisms) in a biopsy sample during transport in a manner which obviates or mitigates deleterious effects of lengthy periods of transport or storage on the success rate of determining the identity of a causative organism behind infections such as osteomyelitis.

According to one aspect, the invention provides a device for preserving causative organisms in a biopsy sample. The device includes a reservoir chamber for containing a transport medium, an outlet operably coupled to the reservoir chamber and having a releasable connector for use in releasably connecting the outlet to a biopsy container housing the biopsy sample, and a dispensing mechanism in mechanical communication with the reservoir chamber, the dispensing mechanism being operable to deliver the transport medium from the reservoir chamber into the biopsy container when the biopsy container is connected to the outlet.

In some embodiments, the outlet is an outlet luer comprising external threads shaped and dimensioned to be complementary to internal threads of a luer connector element of a biopsy syringe.

In some embodiments, the device includes a biopsy syringe, the biopsy syringe having a luer connector element that is internally threaded and complementary to the externally threaded outlet luer.

In some embodiments, the reservoir chamber has a cylindrical portion, and wherein the dispensing mechanism comprises a disc depressible into the cylindrical portion of the reservoir chamber for expelling the transport medium from the reservoir chamber via the outlet luer.

In some embodiments, the device includes at least one stop member coupled to the cylindrical portion movable between a flattened and a proud position, wherein the stop member allows depression of the disc when in the flattened position and prevents the disc from being retracted after being depressed when in the proud position.

In some embodiments, the dispensing mechanism comprises a compressible material around the reservoir chamber, whereby squeezing the compressible material causes the transport medium contained in the reservoir chamber to be expelled via the outlet luer.

In some embodiments, the device includes a luer cap, the luer cap comprising a complimentary threading for anaerobically interfacing with the outlet luer and a plug shaped complimentarily to the outlet luer for plugging the outlet luer.

In some embodiments, the device is used in preserving a bone biopsy sample during transportation or storage.

According to another aspect, the invention provides use of the device for the preservation of a bone biopsy sample.

In some embodiments, the bone sample is for use in determining, the identity of a causative organism of a case of osteomyelitis.

According to yet another aspect, the invention provides a method for preserving organisms in a biopsy sample during transport or storage. The method includes opening a reservoir device containing a transport medium, releasably attaching a biopsy container containing a biopsy sample to the reservoir device in an air-tight manner, dispensing the transport medium from the reservoir device into the biopsy container, and transporting or storing the reservoir device and biopsy container as a sealed unit.

BRIEF DESCRIPTION OF THE DRAWINGS

Other features and advantages of the present invention will be apparent to the person skilled in the art, having regard to the following description and schematic drawings in which.

DETAILED DESCRIPTION

The invention relates to a device and method for supporting the survival of biopsy samples. The device includes means for delivering a transport medium to a biological sample to preserve and support survival of causative organisms as well as means for preventing contamination of the sample during transport or storage.

Embodiments comprise a reservoir device having a reservoir containing a transport medium. The reservoir device has an outlet releasably attachable to a housing containing a biopsy sample in an air-tight manner.

A transport medium contained in the reservoir device can be delivered into the housing by operation of the reservoir device, thereby submersing the biopsy sample in the transport medium to support survival of the causative organisms. The air-tight connection between the reservoir device and the housing prevents contamination of the organisms during transport or storage.

In some embodiments, the combined unit of the reservoir device and housing can be transported as one unit to the laboratory for subsequent analysis.

Figure 1:
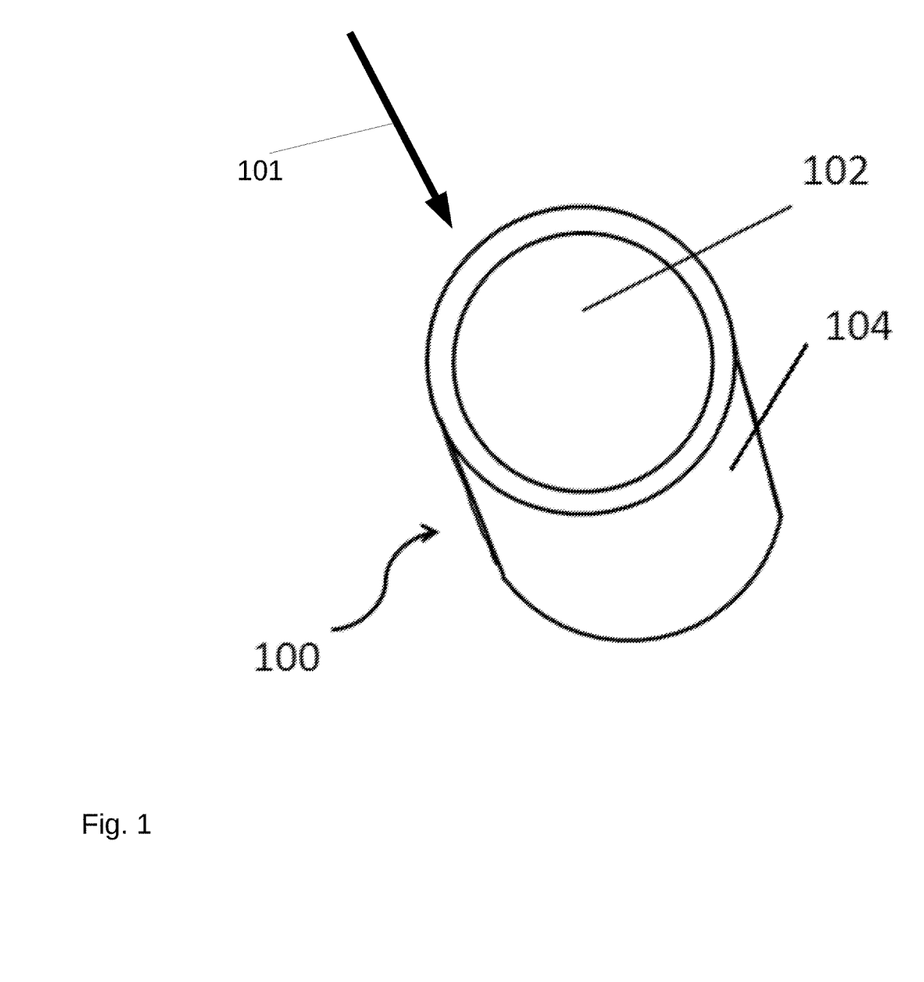
FIG. 1 is a perspective view of a reservoir device for preserving causitive organisms in a biopsy sample, according to a first non-limiting embodiment.

FIG. 1 shows a perspective view of a reservoir device 100, according to a first non-limiting embodiment. The reservoir device 100 comprises a depressible dispensing disc 102 and capsule wall 104. Both the dispensing disc 102 and the capsule wall 104 is made of a firm material, which in this embodiment is a hard plastic made of polyvinyl chloride (PVC).

Figure 2:
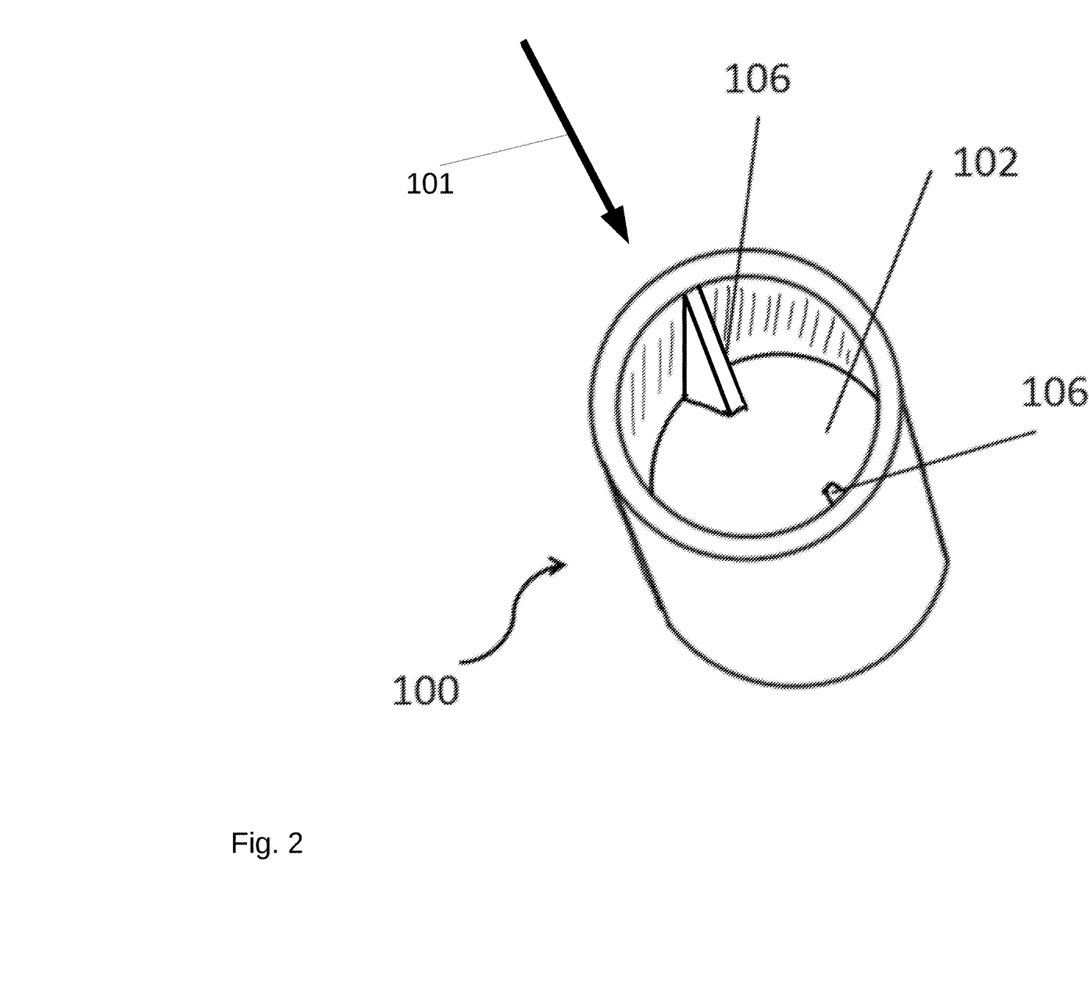
FIG. 2 is a perspective view of the reservoir device of FIG. 1, shown with a dispensing disc depressed to dispense a transport medium.

FIG. 2 shows the reservoir device 100 with the dispensing disc 102 depressed. The dispensing disc 102 is shown depressed into a cylindrical portion of the reservoir device 100. As shown, the reservoir device 100 further comprises stop members 106 for preventing the retraction of the dispensing disc 102 after being depressed. In the example embodiment shown, the stop members 106 comprise a pair of opposing triangular deformable stop members. In a rest position, the stop members 106 extend along the length of the capsule wall 104 toward the dispensing disc 102, biasing the dispensing disc 102 in a direction opposite to a direction of depression 101. As the dispensing disc 102 is depressed, the stop members 106 deform to allow the passage of the dispensing disc 102 in the direction of depression 101, for example, by folding up against the capsule wall 104. After the dispensing disc 102 is depressed past the point of the stop members 106, the stop members 106 revert to their original position and thereby prevent the dispensing disc 102 from moving in the reverse direction after having been depressed.

In the present embodiment, the stop members 106 are made of a hard plastic made of PVC.

Figure 3:
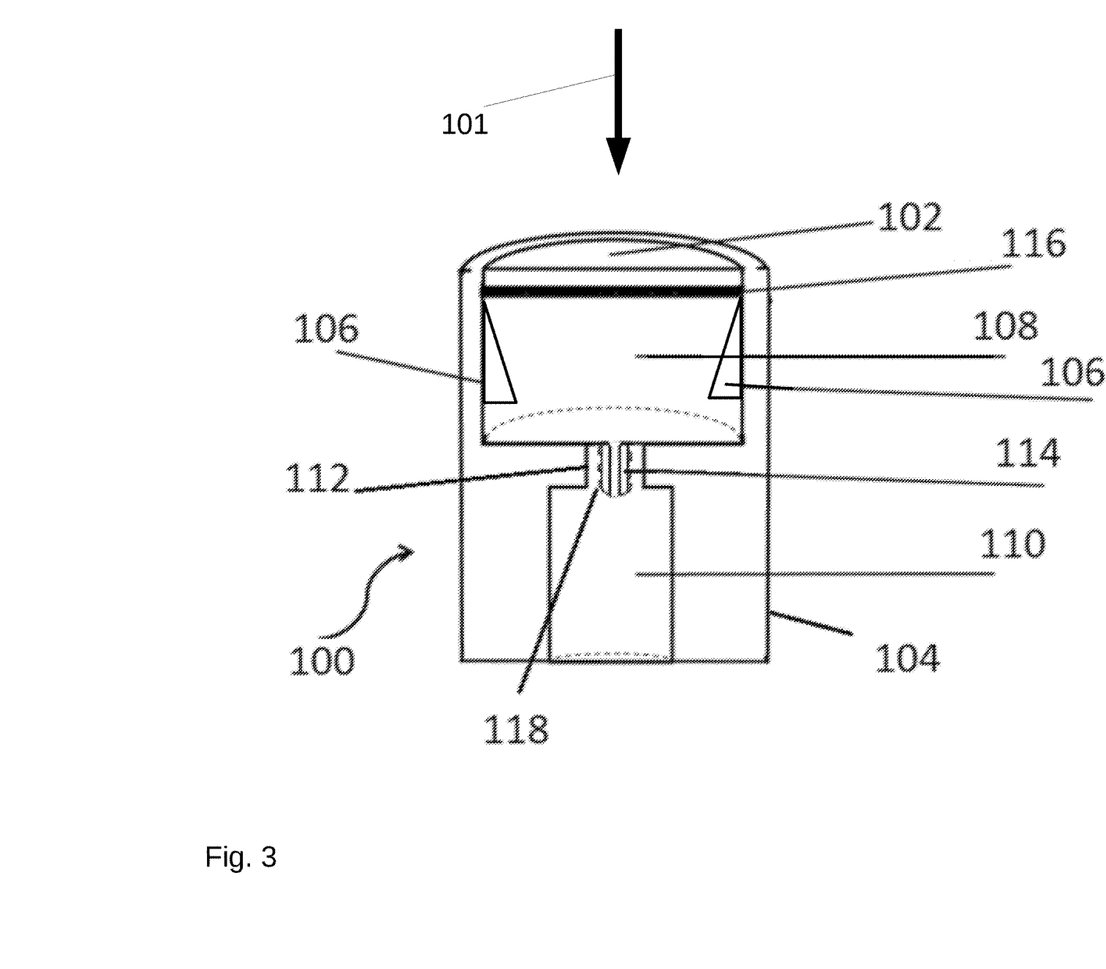
FIG. 3 is a cross-sectional view of the reservoir device of FIG. 1.
Figure 4:
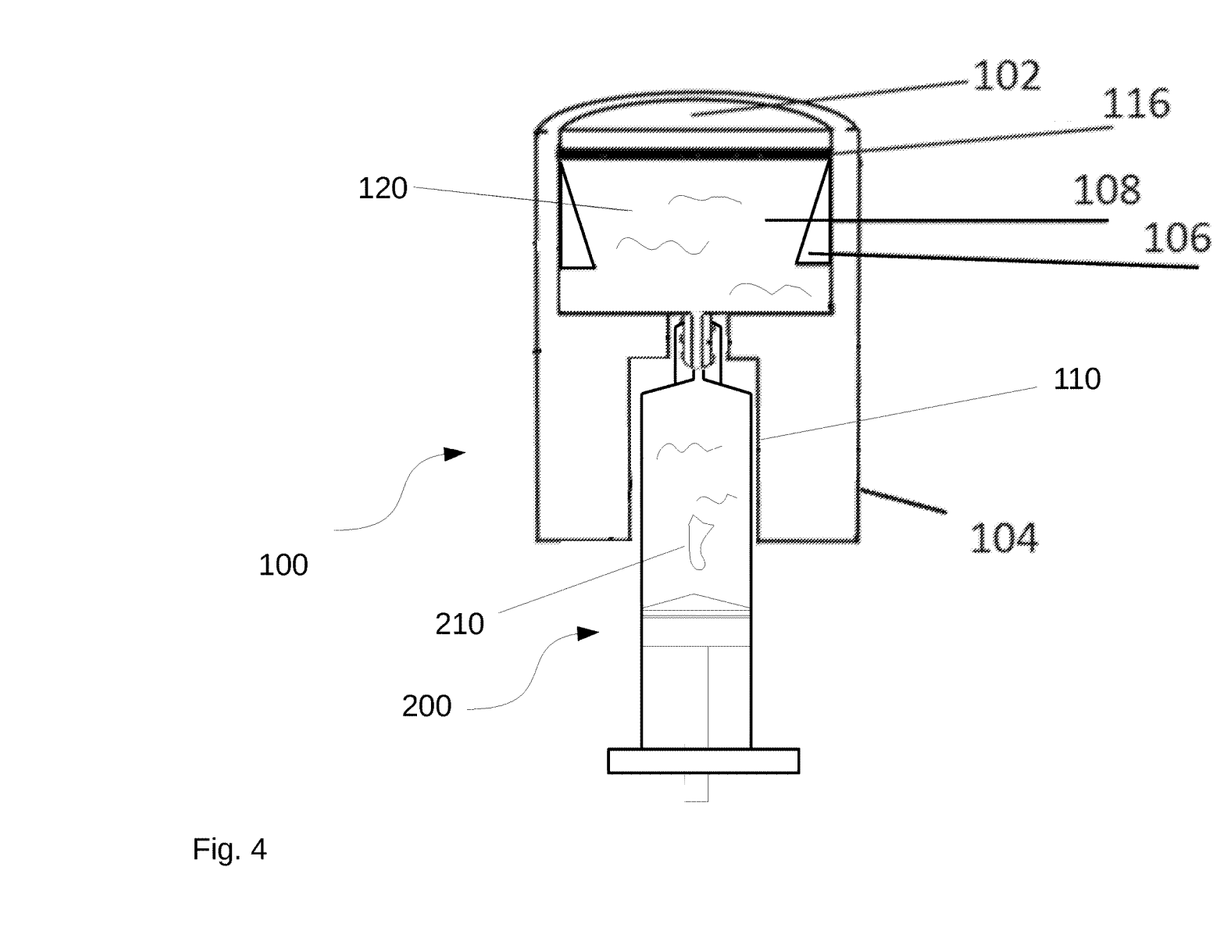
FIG. 4 is a cross-sectional view of the reservoir device of FIG. 1 fitted with an attached syringe.

FIG. 3 and FIG. 4 are cross-sectional views, showing, amongst other things, the reservoir device 100. The reservoir device 100 comprises a reservoir chamber 108 containing a transport medium 120 (shown only in FIG. 4) and a syringe chamber 110 for containing an attached syringe or other attached biopsy container. The reservoir chamber 108 and syringe chamber 110 are connected by a connecting chamber 112, which houses an outlet luer 114 for making the interface between the reservoir device 100 and a attached syringe or other attached biopsy container.

FIG. 4 shows the reservoir device 100 containing the transport medium 120 in the reservoir chamber 108 in preparation for delivery. The device 100 is fitted with a syringe 200 as follows. The outlet luer 114 comprises external threading 118 which is complementary to internal threading on the syringe 200. Thus, the syringe 200 can be screwed on to the outlet luer 114 in an air-tight manner. The syringe 200 contains a biopsy sample 210 for receipt of the transport medium 120.

The dispensing disc 102 is in mechanical communication with the reservoir chamber 108 such that when the dispensing disc 102 is depressed, the transport medium 120 is expelled from the reservoir chamber 108 through the outlet luer 114 and into the syringe 200. In this way, the outlet luer 114 is capable of anaerobically delivering transport medium from the reservoir chamber 108 into the syringe 200. The reservoir chamber 108 is large enough to hold a quantity of transport medium sufficient to completely immerse the biopsy sample.

The reservoir device 100 further comprises a disc seal 116 between the dispensing disc 102 and the reservoir chamber 108 to prevent the transport medium from unintentionally flowing out of the reservoir chamber 108, and to prevent contamination of the transport medium from the outside environment. In this embodiment, the disc seal 116 is made of rubber capable of providing an air-tight seal between the reservoir chamber 108 and the dispensing disc 102.

The reservoir chamber 108 contains a transport medium capable of supporting the survival of an organism in a biopsy sample, such as bacteria, while in transport or storage. In this embodiment, the transport medium is thioglycollate broth with suitable additives and preservatives, including, for example, indicators in the presence of oxygen, such as methylene blue, and other additives including casein peptone, dextrose, soy peptone, sodium chloride, L-cystine, sodium sulfite, agar, vitamin K, hemin, resazurin, yeast extracts, calcium carbonate chips, papaic digest of sybean meal, etc., as would be understood to be an appropriate additive or preservative by the person skilled in the art.

Figure 5:
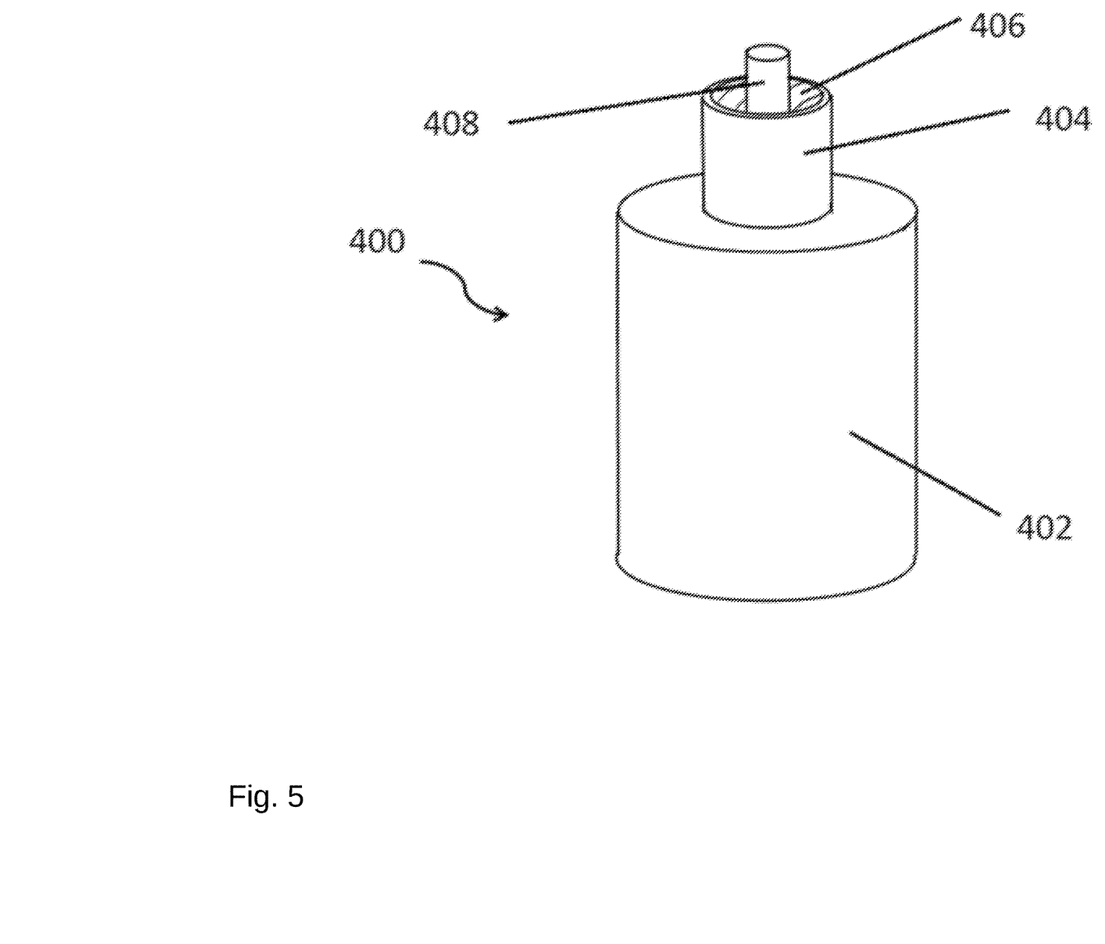
FIG. 5 is a perspective view of a reservoir device luer cap for use with the device of FIG. 1.

FIG. 5 shows a perspective view of a reservoir device luer cap 400, according to a non-limiting embodiment. In the example embodiment, the luer cap 400 comprises a cap body 402, a complementary luer 404 with internal threading 406, and a plug 408. The complementary luer 404 and internal threading 406 are shaped complementary to the outlet luer 114 and the external threading 118 of the reservoir device 100. Furthermore, the plug 408 is shaped as a cylindrical protrusion complementary to the interior of the outlet luer 114 so as to plug into the outlet luer 114 in an air-tight manner. The cap body 402 is preferably shaped complementary to the syringe chamber 110, but of greater length than the syringe chamber 110, so that the luer cap 400 can be easily screwed into and unscrewed from the reservoir device 100.

When the reservoir device 100 is not in use, the luer cap 400 is to be inserted into the syringe chamber 110 so as to seal the reservoir chamber 108, prevent leakage of the transport medium contained within the reservoir chamber 108, and prevent contamination of the transport medium from the outside environment.

Figure 6:
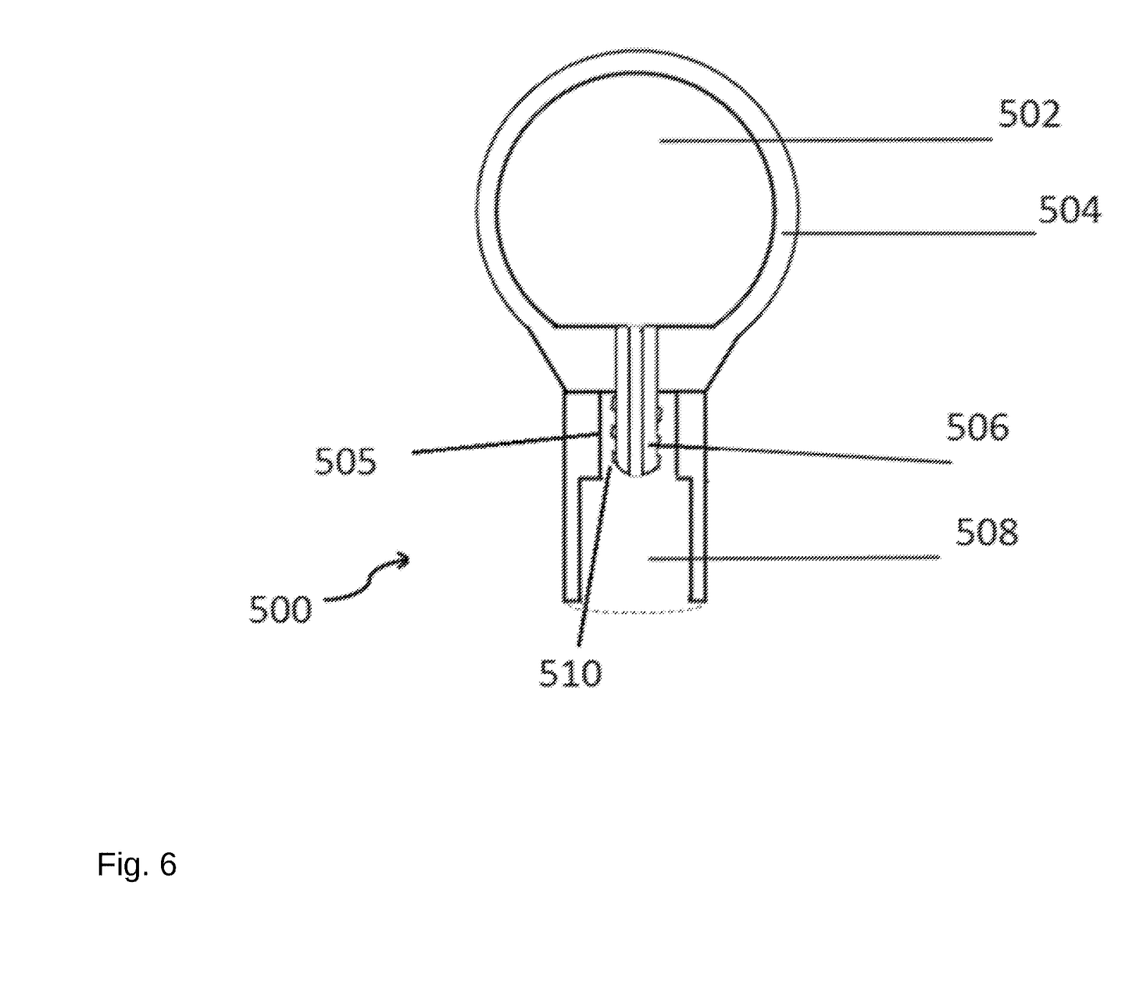
FIG. 6 is a cross-sectional view of a reservoir device for preserving causative organisms in a biopsy sample, according to a second non-limiting embodiment.

FIG. 6 depicts a cross-sectional view of a spherical reservoir device 500 for holding a transport medium within a spherical reservoir chamber 502. In this embodiment, instead of a dispensing disc 102 being depressible to cause a transport medium to be pressed and to flow into a syringe chamber, the reservoir wall 504 is compressible and when compressed or squeezed can cause the contents of the reservoir chamber 502 to be expelled. As with the reservoir device 100, the spherical reservoir device 500 may operate anaerobically or aerobically depending on whether or not air is allowed to enter the chamber 502.

The spherical reservoir device 500 comprises reservoir walls 504, a spherical reservoir chamber 502. As with the cylindrical reservoir device 100, the spherical reservoir device 500 comprises a syringe chamber 508, a connecting chamber 505, and an outlet luer 506 with external threading 510 which can connect with a complementary biopsy container such as a syringe.

Figure 7:
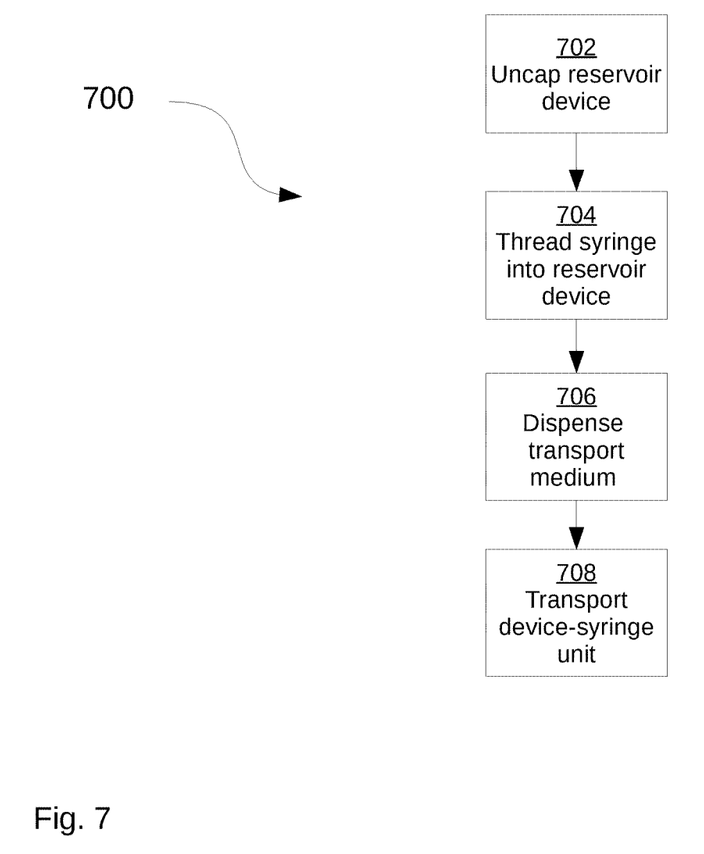
FIG. 7 is a flowchart of a method for preserving causative organisms in a biopsy sample using the device of FIG. 1 or FIG. 6, according to a non-limiting embodiment.

FIG. 7 depicts a flowchart of a method 700 for preserving causative organisms in a biopsy sample, according to a non-limiting embodiment.

At step 702, any cap initially fitted into a reservoir device is removed. A reservoir device may have been fitted with a luer cap for sealing the reservoir device from the environment.

At step 704, the reservoir device is fitted with a syringe containing a biopsy sample to be preserved by attachment a luer on the syringe with a complementary luer on the reservoir device.

At step 706, the transport medium is delivered to the biopsy sample through an anaerobic connection. The transport medium is delivered by a user depressing the transport medium from the reservoir device and retracting the syringe.

At step 708, the reservoir device and syringe are transported as a single sealed unit. Maintaining the connection between the reservoir device and the syringe during transport is for preventing contamination, aerobic or otherwise, of the transport medium-biopsy sample mixture.

Other embodiments of a reservoir device are contemplated, with different dispensing mechanisms, differently shaped reservoir chambers, and different materials.

For example, the person skilled in the art would readily understand that differently shaped reservoir chambers, and different dispensing mechanisms, could be used, provided that a transport medium can be expelled from the reservoir chamber by a dispensing mechanism.

As another example, in other embodiments involving a dispensing disc and a capsule wall, the dispensing disc and capsule wall may be made of the same material, or different materials, including, without limitation, a pliable material such as a soft plastic or rubber material or a combination of a pliable material and a hard material. Furthermore, it is contemplated that variations in stop members, other than triangular stop members, will work to prevent the dispensing disc from moving in the reverse direction after having been depressed.

For example, the capsule walls and stop members could be made of other rigid medical grade plastics, such as acrylonitrile butadiene styrene or polyethylene terephthalate.

For example, the walls of a spherical reservoir device could be made of a soft pliable material such as silicone elastomers or thermoplastic elastomers, or other medical grade elastomer.

As yet another example, the stop members could be of a curved shape. The stop members could also be retractable so as to retract into the capsule walls to allow the dispensing disc to pass in the depression direction, and thereafter extending so as to block the dispensing disc from moving in the reverse direction after having been depressed. In such embodiments, a small spring or other biasing means can be embedded between each stop member and capsule wall to providing the biasing force of the stop members in a direction against the direction of retraction.

As yet another example, in other embodiments involving a dispensing disc and a capsule wall, the disc seal could be made of any other suitable material as would be apparent to the skilled person including liquid silicon rubber, Viton®, ethylene propylene, nitrile, thermoplastics, fluorocarbon materials, perfluoronated materials, or another medical grade elastomer.

Furthermore, the person skilled in the art would readily understand that the reservoir chamber could be releasably connected to other containers or caps.

For example, although the reservoir chamber may be connected by the outlet luer to a syringe containing a biopsy sample, other biopsy containers with complementary shape and threading may also connect with the outlet luer for delivery of the transport medium to a biospy sample.

As another example, although the reservoir device may be sealed by the luer cap prior to use, the reservoir device may be sealed by other means. For example, the reservoir device may be provided assembled with a syringe filled with a biopsy sample for a given length of time, before transportation, ready for delivery of a transport medium.

Other embodiments of a reservoir device with different transport media are contemplated.

For example, in other emboidments, the transport medium can be any medium known to the skilled person such as Fastidious Anaerobe Broth, serum broths, liquid agar, and so forth.

Other embodiments of the use, and methods of use, of a reservoir device are also contemplated.

For example, although it is contemplated that the reservoir device can be used to support the survival of organisms throughout lengthy transportation, it is also contemplated that the reservoir device can be used for other storage scenarios, such as, for example, short-term storage in a laboratory or hospital environment, or storage where movement of samples is frequent.

As another example, although the outlet luer provides for an aneroic connection between the reservoir chamber and a complementarily threaded biopsy container, it is contemplated that in other embodiments the reservoir device can be used to aerobically deliver a transport medium to a biopsy sample without making an attachment through outlet luer. In such embodiments, the transport medium can be expelled from the reservoir chamber to a biopsy sample spaced away from the reservoir chamber by the dispensing disc pressing on the transport medium.

As yet another eaxmple, although reference herein is made to bone biopsies, specifically for the preservation of causative organisms behind a case of osteomyelitis, it will be apparent to the person skilled in the art that the biopsy sample can be of other biological tissues or samples for the analysis of other organisms.

Thus, this specification provides a novel device and method for preserving organisms in a biopsy sample during transport or storage in a manner which obviates or mitigates deleterious effects of lengthy periods of transport on the success rate of determining the identity of an organism.

The scope of the claims should not be limited by the embodiments set forth in the above examples, but should be given the broadest interpretation consistent with the description as a whole.

REFERENCES

1. Sehn J K, Gilula L A. Percutaneous needle biopsy in diagnosis and identification of causative organisms in cases of suspected vertebral osteomyelitis. European Journal of Radiology. May 1062; 81(5): 940-946
2. Garg V, Kosmas C, Young P C, Togaru U K, Robbin M R. Computer tomography-guided percutaneous biopsy for vertebral osteomyelitis: a department's experience. Journal of Neurosurgery. August 1064; 37(2):E10
3. Heyer C M, Al-Hadari A, Mueller K, Stachon A, Nicolas V. Effectiveness of CT-Guided Percutaneous Biopsies of the Spine: An Analysis of 202 Examinations. Academic Radiology. July 1008; 15(7): 901-911
4. Rieneck K, Hansen S E, Karle A, Gutschik E. Microbiologically verified diagnosis of infectious spondylitis using CT-guided fine needle biopsy. APMIS. Aug. 15, 1996; 104(7-8):755-762
5. Lecouvet F, Irenge L, Vandercam B, Nzeusseu A, Hamels S, Gala J. The etiologic diagnosis of infectious discitis is improved by amplification-based DNA analysis. American College of Rheumatology. September 1004; 50(9):2985-2994

What is claimed is:

1. A device for preserving organisms in a biopsy sample, the device comprising:
    a reservoir chamber for containing a transport medium;
    an outlet operably coupled to the reservoir chamber and having a connector element for use in releasably connecting the outlet to a biopsy container housing the biopsy sample;
    a biopsy container chamber in communication with the reservoir chamber via the outlet, the biopsy container chamber having a depth, the biopsy container chamber having a diameter greater than a diameter of the biopsy container, the depth and diameter of the biopsy container chamber dimensioned to contain a portion of the biopsy container when the biopsy container is connected to the outlet; and
    a dispensing mechanism in mechanical communication with the reservoir chamber, the dispensing mechanism being operable to deliver the transport medium from the reservoir chamber into the biopsy container when the biopsy container is connected to the outlet.

2. The device of claim 1, wherein the connector element comprises a first leer connector element, and wherein the biopsy container comprises a biopsy syringe, the biopsy syringe including a second liter connector element complementary to the first leer connector element.

3. The device of claim 2, further comprising the biopsy syringe connected to the outlet.

4. The device of claim 2 wherein the dispensing mechanism comprises a compressible material around the reservoir chamber, whereby squeezing the compressible material causes the transport medium contained in the reservoir chamber to be expelled via the outlet.

5. The device of claim 2 further comprising a liter cap, the liter cap comprising a complementary threading for anaerobically interfacing with the first luer connector element and a plug shaped complementarily to the outlet for plugging the first luer connector element.

6. The device of claim 1 wherein the reservoir chamber has a cylindrical portion, and wherein the dispensing mechanism comprises a disc depressible into the cylindrical portion of the reservoir chamber for expelling the transport medium from the reservoir chamber via the outlet.

7. The device of claim 6 further comprising at least one stop member coupled to the cylindrical portion movable between a flattened and a proud position, wherein the stop member allows depression of the disc when in the flattened position and prevents the disc from being retracted after being depressed when in the proud position.

8. A method for preserving organisms in a biopsy sample using the device of claim 1, the method comprising:
    releasably attaching a biopsy container containing a biopsy sample to the device in an air-tight manner, a portion of the biopsy container being received by the biopsy container chamber of the device; and
    dispensing the transport medium from the reservoir chamber of the device into the biopsy container.

9. The method of claim 8, further comprising, prior to releasably attaching the biopsy container containing the biopsy sample to the device, removing a luer cap from interfacing with the connector element of the outlet of the device to open the device.

10. The method of claim 8, further comprising transporting or storing the device and the biopsy container as a sealed unit.

11. The method of claim 8, wherein the bone biopsy sample is preserved for use in determining an identity of a causative organism of a case of osteomyelitis.

* * * * *